United States Patent [19]

Klippert

[11] 4,012,954
[45] Mar. 22, 1977

[54] TESTING APPARATUS FOR LIGHT- AND WEATHER-RESISTING PROPERTIES

[75] Inventor: Hans Ulrich Klippert, Hanau am Main, Germany

[73] Assignee: Original Hanau Quarzlampen GmbH, Hanau am Main, Germany

[22] Filed: Jan. 20, 1976

[21] Appl. No.: 650,644

[30] Foreign Application Priority Data

Jan. 21, 1975 Germany .......................... 2502239

[52] U.S. Cl. ............................... 73/150 R; 73/159; 73/432 SD
[51] Int. Cl.[2] ....................................... G01N 17/00
[58] Field of Search ............... 73/150, 159, 432 SD
[56] References Cited

UNITED STATES PATENTS 1,827,530  10/1931  Grand ............................ 73/432 SD 3,686,940  8/1972  Kockott .............................. 73/150

*Primary Examiner*—S. Clement Swisher
*Attorney, Agent, or Firm*—Sughrue, Rothwell, Mion, Zinn & Macpeak

[57] ABSTRACT

This invention relates to a testing apparatus for light- and weather-resisting properties, with a sample room having a gas discharge radiator arranged therein, as well as to a mirror placed between this radiator and the samples, selectively reflecting the infrared portion of the radiation and being permeable to the visible and ultraviolet portion thereof, and to an additional mirror, selectively reflecting the visible and the ultraviolet portion of the radiation and transmitting the infrared portion thereof.

25 Claims, 4 Drawing Figures

TESTING APPARATUS FOR LIGHT- AND WEATHER-RESISTING PROPERTIES

DESCRIPTION OF THE PRIOR ART

Organic material and auxiliary means, as e.g. textiles, rubber, leather, artificial material, lacquers and coloring matters will change their properties as well as their morphological structure under the influence of sunlight and other climatic factors, as there are temperature, humidity and rain. As a result of these molecular processes, there will be change of the macroscopic, mechanic, thermic, electric and optical properties, as for example, mechanic stability, heat conductibility, electric conductibility, as well as the electricity constant, transmission and the color of the material. The synthetic coloring matters, which in the first phase of their development have still been rather instable to the sunlight, necessitated a test for light- and weather-resisting properties of the colorations. The tests whereby the material was exposed to the influence of sunlight, and climatic conditions have already many times been replaced by a simulation of the sunlight or, respectively, the climatic conditions.

The conventional devices developed for a simulated testing of the light-and weather-resisting properties of materials have a centrally arranged radiator, being a gas discharge radiator in the more modern devices and centrally arranged in the sample room proper, whereby the samples are arranged around this radiator either standing or suspended. Concerning their outer dimensions, these devices are configured extremely voluminous and clumsy. In addition thereto, the radiation reflectors or, respectively, the initially mentioned selectively reflecting mirrors necessitate a relatively complicated construction. Further, with these devices, where the samples are arranged around die radiation source, the infrared radiation must be eliminated via an absorber, which has to be cooled off by a cooling agent. Thus these devices can only be manufactured at a considerable expense or cost. Moreover, the accessability of the sample room is obstructed, the more so as the sample room must be closed in view of the different climatic conditions that must be strictly adhered to, and thus one must either provide for very many doors or, in the event the samples are rotable around the central radiation source, they must be individually rotated to face one specific door. In this respect the replacement of the samples exacts a considerable expenditure, which could be avoided if such an arrangement of the samples were not absolutely necessary.

An apparatus for producing artificial climatic conditions has already become known (U.S. Pat. No. 1,827,530), in which the substrates to be treated are placed on an essentially horizontal table and then irradiated by quartz lamps, for example. Thereby the desired climatic conditions are simulated by means of rather expensive equipment.

OBJECTS OF THE INVENTION

It is the object of the invention to provide a testing apparatus for light- and weather-resisting properties of the initially mentioned kind, which is simple with respect to construction and of little extent concerning its outer dimensions, which at the same time permits an effective and exact light- and weather-resisting test under favorable conditions, which simultaneously produces variable climatic conditions, and which provides an easy access to the interior of the apparatus.

SUMMARY OF THE INVENTION

According to the invention, this object is realized in that samples in a manner already known as such are placed on an essentially horizontal support, and that the sample room above this support consists of an elongated reflector channel of parabolic section, sealed at its extremities by faces of parabolic circumference, whereby the lateral faces of the reflector channel, being parabolic in assembled condition, are made of elastic pliable sheet metal, which adopts the parabolic shape when applied to the parabolic circumference of the front faces.

Due to the special configuration of the side wall of the reflector channel that can be connected with a door, and the plain arrangement of the sample support, an advantageous and easy access is obtained with regard to a quick replacement of the samples. In that the side wall of the reflector channel consists of a simple elastic sheet metal not premolded, contrary to such reflectors known so far, there will be no more molding costs. Thus for the manufacture of a parabolic reflector channel, all that is left is a simple plate part treatment. In addition thereto, individual reflector parts can be easily exchanged if they have become dull during operation, so that it is no longer necessary to replace the entire reflector, a rather complicated work by the way. As a simple punched part, the front faces of the reflector channel present a parabolic circumference, against which rest the side faces of the reflector channel, without having to be premolded as mentioned above. Since the side wall of the reflector channel is made of elastic sheet metal, it can deform itself if the pivot of the door is not in the fixation point of the upper edge of the side wall, and again rest against the parabolic circumference of the front face in an advantageous manner if the door is closed again.

Thereby the pivot of the elastic side wall of the reflector channel and that of the door can be locally separated from each other, whereby the lower edge of the side wall is movably carried in the door. Thus in an especially easy manner one obtains a practical access and likewise providing sufficient space to the sample room.

In a preferred embodiment the gas discharge radiator, being a xenon radiator in order to simulate the sunlight as exactly as possible, is located in the focal line of the reflector channel of parabolic section. Thereby in an especially simple and efficient manner, the initially mentioned selectively reflecting mirrors can be arranged around the radiator, whereby the mirror selectively reflecting the infrared portion of the radiation, but permeable to the visible and ultraviolet portions, can be configured as a third of a tube curved away from the xenon radiator in the direction of the samples, and arranged between the upper edges of the side walls of the reflector. In a similar manner, the additional mirror, selectively reflecting the visible and ultraviolet portion of the radiation and permeable to the infrared portion thereof, can be arranged on the side of the xenon radiator not facing the samples in a rooflike manner, such as to lean tangentially against the imaginary elongation of the parabolic reflector. Thereby an optimum reflection of the ultraviolet rays or, respectively, of the visible radiation portion is obtained. By this arrangement, the infrared portion of the radiation can be carried off upwards in an especially simple manner.

Due to the special configuration of the sample room, the samples and the xenon radiator can be properly cooled by a biwired air cooling, whereby the cooling air for the xenon radiator is sucked in from above and that for the samples from below, whereby the cooling air can be conducted directly along the xenon radiator or, respectively, be admitted into one of the faces of the reflector channel, without requiring any troublesome cooling air conduits, which would complicate the entire construction.

In order to obtain a cooling of the samples as uniformly and effectively as possible, the air inlet and outlet slits in the faces of the reflector channel are adjusted to the width of the sample carrier, whereby moreover the air inlet slit is arranged somewhat higher than the air outlet slit in relation to the supporting plane for the samples. In addition thereto, the cooling air can be turbulently admitted in order to obtain an optimally uniform cooling.

In order to be able to arrange as many samples as possible on one sample support, and at the same time to allow a good comparison of the surfaces of the samples exposed to the rays with those not exposed to rays by being covered up, the samples, e.g. color patterns of textile fabric, can be arranged in an overlapping manner.

In order to increase the versatile usability of the device, and especially in regard to the testing conditions, and to reduce the size of the entire device, the horizontal support can be configured as a removable tin tub, which can be lodged in a frame via a floor opening in the sample room.

In order that the surface to be tested is always exactly on the same level even if samples are of different thickness, the tin tub can be configured relatively deep, whereby the samples by correspondingly adjusted supports of different thickness must be brought to the proper level.

In order to create humid test conditions, the tub can be made floodable in an especially simple manner and thereby be adjustable at a certain water level, whereby the flooding installation is directly fastened at the tub and thus can be placed into the device together with the tub. Insofar the entire apparatus does not have to be provided in advance with all equipment in order to simulate the different climatic conditions in the sample room.

In order not to whirl up or press away the water during the flooding operation, the aeration into the sample room can for example be automatically stopped while flooding via a magnetic control and be switched on again together with the flowing-off of the water.

To obtain an especially effective cooling, the tube can have a double bottom, whereby the lower part of the tube is floodable by means of cooling agents. If thereby the intermediate bottom allows a good heat transition, then a good and uniform cooling of the samples can be effected from below. In order to obtain optimal results from this cooling operation, the lower part of the tub can present a labyrinth arrangement through which the cooling agent can be led.

Finally, in order to further increase the cooling, the cooling air feed from above onto the samples can be switched in simultaneously with the lower bottom cooling. In this manner, by units kept separately from the apparatus but easily insertable into the same, favorable conditions have been provided for bringing about the different climatic conditions and to make the basic apparatus of an especially simple construction.

Further details, features and advantages of the invention will be apparent upon consideration of the following description of the embodiment examples in conjunction with the annexed drawings.

DETAILED DESCRIPTION OF A PREFERRED EMBODIMENT

Figure 1:
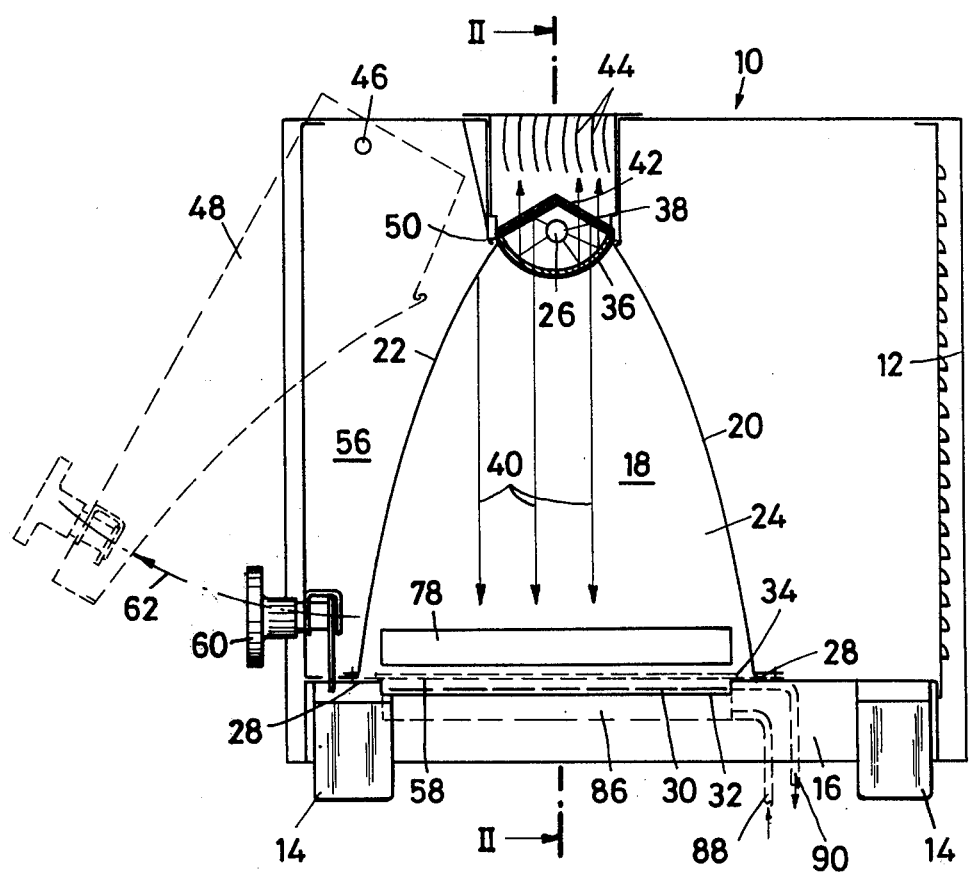
FIG. 1 is a schematic section through a testing apparatus for light- and weather-resisting properties taken along line I—I of FIG. 2.

The testing apparatus 10 for light- and weather-resisting properties as presented in a sectional view on FIG. 1, consists essentially of a housing 12, a lower part 16 provided with supports 14 on the four corners thereof, as well as a sample room 18. This sample room 18 is formed by a reflector channel of parabolic section, being limited laterally by a rear side wall 20, a front side wall 22 as well as by front walls 24. The side walls 20 and 22 are made of an elastically ductile and simple stamped out sheet-metal, which adopts its parabolic shape by putting it against the parabolic contour of the front walls 24. The rear side wall 20, as well as the front walls 24, are rigidly mounted on the housing but can be detached in case of replacement. The sheets do not join to present a complete parabolic shape but rather are intermittently configured in the range of the focal point. Within this area, i.e. in the focal line of the reflector channel, there is a gas discharge radiator 26, being a xenon radiator in order to simulate a sunlight as realistic as possible.

The bottom of the sample room in the lower part 16, except for a rectangular and projecting ridge 28, is open-formed. In this opening, a tub 32 lodging samples 30 is arranged in such a manner that a collar 34 of this tub is supported by the ridge 28.

Mirrors are arranged around the xenon radiator 26, whereby the mirror 36 being arranged between the radiator 26 and the samples 30, which selectively reflects the infrared portion of the radiation and is permeable to the visible as well as the ultraviolet portions of the radiation, is configured like a third of a tube in such a manner that its extremities join the upper edges of the side walls 20 and 22. On the side of the xenon radiator 26 not facing the samples, a mirror 38 is arranged in form of a roof, and that in such a manner that the mirror 38 is tangent to the imaginary elongation of the parabola. The ultraviolet portions of the radiation, reflected by the mirror 38 or, respectively, by the side walls 20 and 22 configured as reflectors, are indicated by the arrows 40. This portion of the radiation immediately hits the samples 30. The infrared portion of the radiation, which directly passes through the mirror 38 or, respectively, is reflected by the mirror 36, is indicated by the arrows 42 and upwards reaches the open air. Perpendicularly arranged sheets 44 do not obstruct the emerging of the infrared radiation but prevent a blinding of the operator.

The sample room is accessible via a door 48 pivoting about a swivel point 46. For this purpose, the front side wall 22 is loosely hinged to the top of the door 48 and clamped at the bottom.

The opening operation of the door 48 is done as follows: via the locking handle 60 the locking is at first released and then the door 48 is pivoted around the gravity center 46 by the locking handle 60, like it is indicated in FIG. 1 by the arrow 62. During this swivelling operation of the door, the front side wall 22 displaces itself essentially around the upper edge 50. In addition thereto, the front side wall 22 abandons its parabolic shape due to its elastic ductility.

When closing the door, the door itself automatically presses the front side wall 22 against the parabolic contour of the front walls, so that, following the locking operation, the front side wall 22 resumes its final parabolic shape.

In this manner, the reflector parts can be configured as simple punched parts merely having to be edged, which furthermore can be individually exchanged as compared to a deep-drawn part.

Likewise the sample tub 32 can be exchanged due to the relatively large opening, which can be necessary especially when samples of a greater thickness shall be exposed to rays, whereby at any rate the surface of these samples to be tested should be on the same level. However, from the beginning one can use a deep tub, as indicated in broken lines on FIG. 1, whereby for samples of different thickness correspondingly adjusted supports can be placed in the tub, so that the surfaces of the samples to be tested each time observe the same distance in regard to the xenon radiator.

Figure 2:
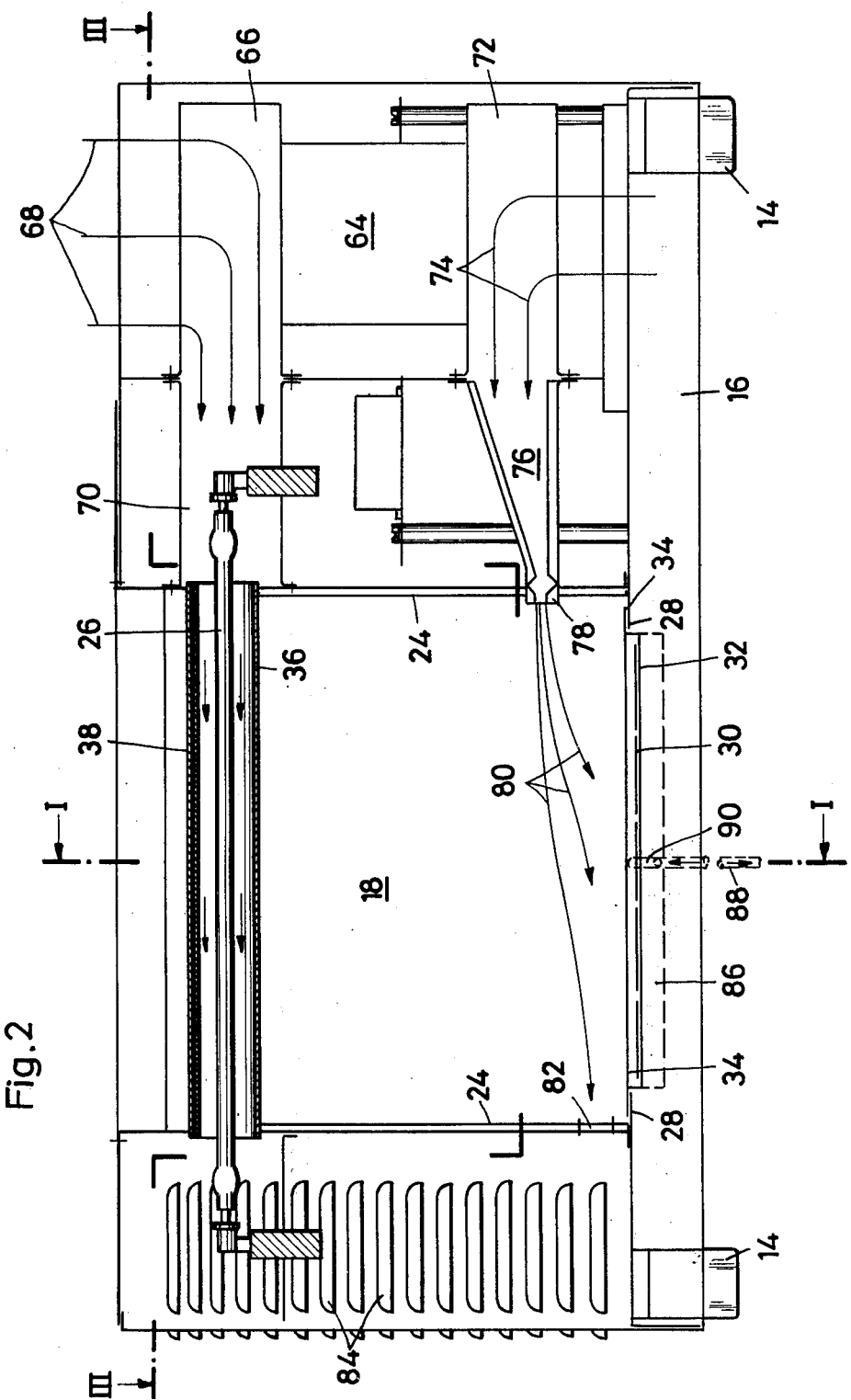
FIG. 2 is a schematic longitudinal section through the apparatus taken along line II—II of FIG. 1.

In order to create the desired climatic conditions, especially for the cooling of the samples or, respectively, of the sample area and for the cooling of the xenon radiator 26, there is provided a double blower in the housing in the projection of the reflector channel 18, driven by a central motor 64, whereby the upper blower 66 is sucking in axially cooling air according to the arrows 68 in FIG. 2, and is blowing it off radially in such a manner that the cooling air, via an exhaust channel 70, is led along the xenon radiator 26 and flowing round the same.

A lower blower 72 likewise axially sucks in cooling air according to the arrows 74 and blows it into the sample room itself via an exhaust channel 76, horizontally enlarging and vertically narrowing, as well as through a supply air slit 78 located in one of the front walls 24. Thereby the exhaust channel 76 is configured like a nozzle in the area of the supply air slit, so that the cooling air gets into the sample room in form of a turbulent flow. This cooling air flow in the sample room is indicated on FIG. 2 by the arrows 80. Through an outgoing air slit 82 the cooling air leaves the sample room and reaches a part of the housing 10 opposite to the blower chamber. The air inlet slit 78 is located on a higher level than the outgoing air slit 82, which means that the air inlet slit 78 is located at a greater distance to the samples than the outgoing air slit 82. The effect hereof is that the cooling air, which presents the lowest temperature when entering the sample room, is then farthest away from the sample, and at the end of the sample room in direction of flow, is next to the samples. Thereby a uniform cooling of all the samples in the tub is obtained. Finally the cooling air, via the ventilation gills 84, gets outside the device 10.

In order to increase the possibility of the climatic conditions, a special tub 86 can be arranged in the opening of the bottom in the sample room 18, as represented in broken lines on FIGS. 1 and 2, being provided with a feeding channel near the bottom and with an outlet channel 90 on the level of the sample surface. Via a pump, not represented in detail, the tub 86 can be flooded with water by means of the feedline 88, up to the overflow opening of the outlet channel 90, whereby the samples are moistened. At the same time the cooling air current 74, 80 can be interrupted, so that the water will not be pushed away from the samples. This control can be effected automatically, e.g. via a magnetic lock, so that the cooling air current is switched off during the flooding and again switched on when draining the water off the tub.

The conduits 88 and 90, as well as the pump, can be directly connected with the tub, and as such are stored separately from the testing apparatus itself, so that the testing apparatus itself does not have to be of unnecessarily complicated and voluminous construction in order to produce the different climatic conditions. Upon opening the door 48, the tub can be easily lodged in the bottom opening of the sample room.

Figure 4:
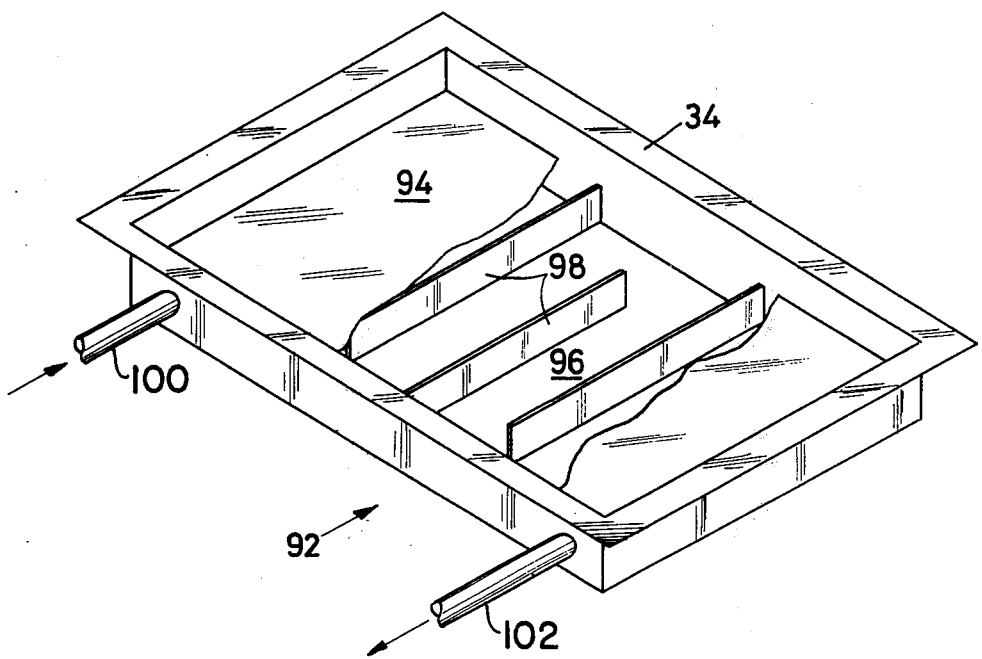
FIG. 4 is a schematic partly cut open view of a sample tub with lower bottom cooling.

To cool the samples, one can likewise use a double tub 92 as represented on FIG. 4, which also has a collar 34 and at the same time an intermediate bottom 94. In a preferable manner, in from of meanders, one can arrange sheets 98 between the bottom 96 and the intermediate bottom 94 in such a manner that a meandering guide will result within these two bottoms. Due to the fact that a feeding channel 100 as well as a drain channel 102 are arranged, the interspace can be flooded in such a manner that the water can continuously flow in a winding course. Thereby the intermediate bottom carrying the samples 30 is cooled in an especially uniform manner, and that the more the better the thermal conduction coefficient is in the intermediate bottom 94. In this case, too, the tub can be lodged in the device as a self-contained unit.

However, simultaneously with this cooling, a cooling from above by means of the blower 72 can be effected.

In order to improve certain desired climatic conditions in the immediate vicinity of the samples, the various tubs can be covered by a quartz glass cover 58, as shown in broken lines on FIG. 1, which freely transmits the ultraviolet radiation. For this purpose, the covering must be as tight as possible.

Figure 3:
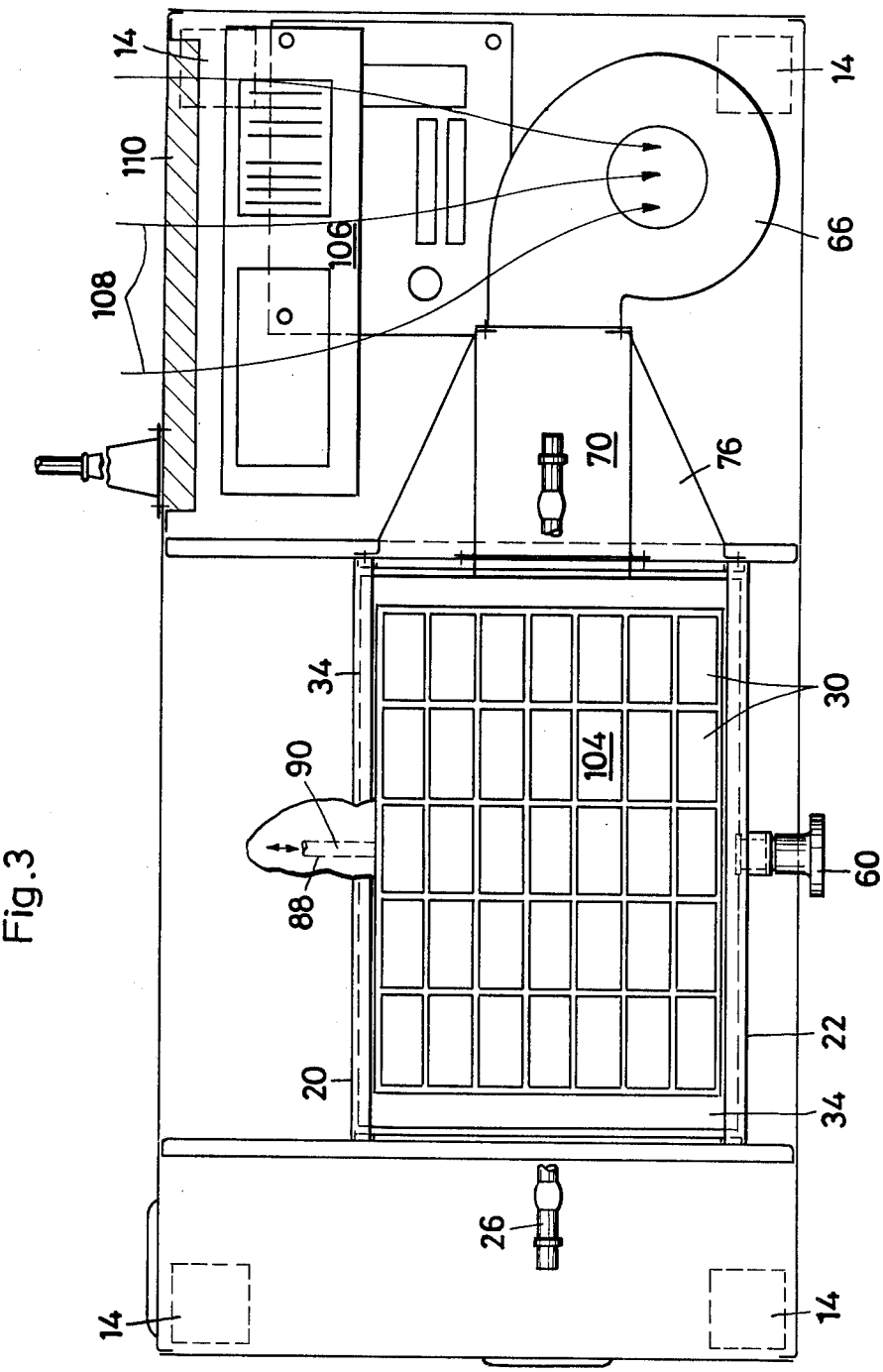
FIG. 3 is another schematic longitudinal section through the apparatus taken along line III — III of FIG. 2.

According to the representation on FIG. 3, the samples 30 can be configured in such a manner that they are coated with different cloth strips 104 of different color and of different material. For space-saving reasons, the samples 30 can also be arranged in the tub in an overlapping manner, which further offers the advantage that the overlapped portion of the sample surfaces is not exposed to radiation and thus an optical comparison after the test can be made in order to find out in how far the color effect was impaired.

In the space left in the housing adjacent to the blower unit, there is placed the complete electrical or, respectively, electronical installation 106, and especially a trigger- and topping device. To cool these devices, according to the representation on FIG. 3, the cooling air, indicated by the arrows 108, can be sucked in in such a manner that at first it brushes past the electronic installation 106, and in particular the cooling air can thereby pass through a filter 110 before entering the housing.

Due to the exchangeability of the sample carrier, the apparatus can be adjusted to the most different conditions while being of compact construction, without having to accommodate all the required auxiliary devices at the same time. In addition thereto, by the most simple construction of the reflector in the sample room, as well as by the possibility of exchanging individual parts of the reflector in case they had become blind, there is guaranteed an extremely favorable and uncomplicated access to the apparatus.

I claim:

1. Testing apparatus for light- and weather-resisting properties, comprising a sample room and a gas discharge radiator arranged in the sample room, as well as a mirror arranged between the radiator and the samples, selectively reflecting the infrared portion of the radiation and permeable to the visible and ultraviolet portions thereof, and an additional mirror, selectively reflecting the visible and ultraviolet portions of the radiation and permeable to the infrared portion, characterized by the facts that the samples (30), in a manner already known as such, are placed on an essentially horizontal support (32, 86, 92) and that the sample room located above the support is composed by an oblong reflector channel (18) of parabolic section, of which the extremities are shut off by front walls (24) of parabolic contour; and the side walls (20, 22) of the reflector channel (18), being parabolic in operational condition, are made of elastic ductile sheet-metal, which assumes the parabolic shape when applied to the parabolic contour of the front walls (24).

2. Testing apparatus for light- and weather-resisting properties according to claim 1, characterized by the fact that the front parabolic reflector wall (22) is pivotable together with a door (48).

3. Testing apparatus of light- and weather-resisting properties according to claim 2, characterized by the fact that an upper edge (50) of the reflector wall is movably arranged on the door (48) and the lower edge (52) rigidly mounted.

4. Testing apparatus of light- and weather-resisting properties according to claim 1, characterized by the fact that that the gas discharge radiator (26) is a xenon radiator which is arranged in the focal line of the reflector channel (18) of parabolic section.

5. Testing apparatus of light- and weather-resisting properties according to claim 4, characterized by the fact that the mirror selectively reflecting the infrared portion of the radiation but permeable to the visible and ultraviolet portion thereof is configured as a third of a tube (36), curved away from the xenon radiator towards the samples (30), being arranged between the upper edges of the reflector side walls (20, 22).

6. Testing apparatus of light- and weather-resisting properties according to claim 4, characterized by the fact that the additional mirror selectively reflecting the visible and ultraviolet portions of the radiation and permeable to the infrared portion (38) is arranged on that side of the xenon radiator not facing the samples (30) in rooflike configuration in such a manner that is leans tangentially against the imaginary elongation of the parabolic reflector.

7. Testing apparatus of light- and weather-resisting properties according to claim 1, characterized by means for conveying the infrared portion (42) of the radiation off upwards.

8. Testing apparatus of light- and weather-resisting properties according to claim 4, characterized by means for cooling the samples (30) and the xenon radiator comprising a double-lined air cooling system.

9. Testing apparatus of light- and weather-resisting properties according to claim 8, characterized by means for sucking the cooling air (68) for the xenon radiator (26) in from above and for leading it along the xenon radiator (26).

10. Testing apparatus for light- and weather-resisting properties according to claim 8, characterized by means for sucking the cooling air (74) for the samples (30) in from below and for admitting it via an air inlet slit (78) to one of the front faces (24) of the reflector channel (18) and then for eliminating it from the other front face (24) through an outgoing air slit (82).

11. Testing apparatus of light- and weather-resisting properties according to claim 10, characterized by the fact that the air inlet and outlet slits (78, 82) are adjusted to the width of the sample carriers.

12. Testing apparatus of light- and weather-resisting properties according to claim 10, characterized by the fact that the air inlet slit (78) is arranged at a higher level than the outgoing air slit (82) in relation to the supporting plane for the samples (30).

13. Testing apparatus of light- and weather-resisting properties according to claim 9, characterized by means for turbulently admitting the cooling air (80).

14. Testing apparatus of light- and weather-resisting properties according to claim 1, characterized by means for overlappingly arranging the samples (30).

15. Testing apparatus for light- and weather-resisting properties according to claim 14, characterized by means for coating the bordering strips of the samples (30) in the marginal area in order to avoid any whirling-up in the air current.

16. Testing apparatus of light- and weather-resisting properties according to claim 1, characterized by the fact that the horizontal support is an exchangeable tin tub (32) which is lodged in a frame through a bottom opening in the sample room.

17. Testing apparatus of light- and weather-resisting properties according to claim 16, characterized by means for adjusting the depth of the tub (32) to the hight of the samples in such a manner that the surface to be tested is always on the same level.

18. Testing apparatus of light- and weather-resisting properties according to claim 16, characterized by means for placing supports of different thickness in the tube (32) in order to exactly level the surface of the samples (30).

19. Testing apparatus of light- and weather-resisting properties according to claim 16, characterized by means for flooding and adjusting the tub (82) to a certain water level.

20. Testing apparatus of light- and weather-resisting properties according to claim 19, characterized by the fact that the flooding installation, independently from the other devices, is only connected with the exchangeable tub (86).

21. Testing apparatus of light- and weather-resisting properties according to claim 19, characterized by means for automatically switching off the ventilation (74) to the sample room (18) during the flooding and for switching it on again together with the draining of the water.

22. Testing apparatus of light- and weather-resisting properties according to claim 16, characterized by the fact that the tub (92) is provided with an intermediate bottom (94), whereby the lower part of the tub can be flooded with cooling agents.

23. Testing apparatus of light- and weather-resisting properties according to claim 22, characterized by the fact that the lower part of the tub presents a labyrinth arrangement through which the cooling water can be led.

24. Testing apparatus of light- and weather-resisting properties according to claim 23, characterized by means for switching on the cooling air from above onto the samples simultaneously with the cooling of the lower bottom.

25. Testing apparatus of light- and weather-resisting properties according to claim 16, characterized by the fact that the tub (32, 86, 92) is covered with a quartz glass cover (58).

* * * * *